US008481499B2

(12) United States Patent
Watkins et al.

(10) Patent No.: US 8,481,499 B2
(45) Date of Patent: *Jul. 9, 2013

(54) BLOCKADE OF GAMMA-SECRETASE ACTIVITY TO PROMOTE MYELINATION BY OLIGODENDROCYTES

(75) Inventors: Trent Alan Watkins, Palo Alto, CA (US); Ben A. Barres, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 125 days.

This patent is subject to a terminal disclaimer.

(21) Appl. No.: 13/066,930

(22) Filed: Apr. 27, 2011

(65) Prior Publication Data
US 2011/0251133 A1    Oct. 13, 2011

Related U.S. Application Data

(63) Continuation of application No. 11/705,909, filed on Feb. 13, 2007, now Pat. No. 7,973,011.

(60) Provisional application No. 60/773,191, filed on Feb. 13, 2006.

(51) Int. Cl.
*A61K 38/55*     (2006.01)
(52) U.S. Cl.
USPC ........ 514/20.1; 514/17.8; 514/17.9; 514/44 A
(58) Field of Classification Search
None
See application file for complete search history.

(56) References Cited

U.S. PATENT DOCUMENTS

| 4,963,557 A | 10/1990 | Badger et al. |
| 2008/0233132 A1 | 9/2008 | Miller et al. |

FOREIGN PATENT DOCUMENTS
WO    WO 2005073250 A2 *    8/2005

OTHER PUBLICATIONS

Cui et al., "NB-3/Notch 1 pathway via deltex1 promotes neural progenitor cell differentiation into oligodendrocytes", J. Biol. Chem., 2004, 279(24):25858-65.
Dovey; et al., "Functional gamma-secretase inhibitors reduce beta-amyloid peptides levels in brain", Journal of Neurochemistry (2001), 76:173-181.
Geling; et al., "A gamma-secretase inhibitor blocks Notch signaling in vivo and causes a severe neurogenic phenotype in zebrafish", EMBO reports (2002), 3(7):688-694.
Genoud; et al., "Notch1 control of oligodendrocyte differentiation in the spinal cord", The Journal of Cell Biology (2002), 158(4):709-718.
Givogri; et al., "Central Nervous System Myelination in Mice With Deficient Expression of Notch1 Receptor", Journla of Neuroscience Research (2002), 67:309-320.

Hohlfeld, "Myelin failure in multiple sclerosis: Breaking the spell of Notch", Nature Medicine (2002), 8(10):1075-76.
Hu; et al., "F3/Contactin Acts as a Functional Ligand for Notch during Oligodendrocyte Maturation", Cell (2003), 115:163-175.
John; et al., "Multiple sclerosis: Re-expression of developmental pathway that restricts oligodendrocyte maturation", Nature Medicine (2002), 8(10):1115-1121.
Jurynczyk; et al., "Inhibition of Notch signaling enhances tissue repair in an animal model of multiple sclerosis", Journal of Neuroimmunology, Dec. 30, 2005, 170(1):3-10, published electronically on Nov. 14, 2005.
Kimberly et al., "Gamma-secretase is a membrane protein complex comprised of presenilin, nicastrin, Aph-1, and Pen-2", Proc. Natl. Acad. Sci. USA, 2003, 100(11):6382-6387.
Lai; et al., "Implication of gamma-secretase in neuregulin-induced maturation of oligodendrocytes", Biochemical and Biophysical Research Communications, Feb. 6, 2004, 314(2):535-542.
Lanz et al., "Studies of Abeta pharmacodynamics in the brain, cerebrospinal fluid, and plasma in young (plaque-free) Tg2576 mice using the gamma-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575).", J Pharmacol Exp Ther., 2004, 309(1):49-55.
Leissring et al., "A Physiologic Signaling Role for the Gamma-Secretase-Derived Intracellular Fragment of APP", Proc Natl Acad Sci USA, 2002, 99(7):4697-702.
Li et al., "Photoactivated gamma-secretase inhibitors directed to the active site covalently label presenilin 1", Nature, 2000, 405(6787):689-94.
Lundkvist; et al., "gamma-Secretase: a complex target for Alzheimer's disease", Current Opinion in Pharmacology (2007), 7:112-118.
McLendon, "Cell-free assays for gamma-secretase activity", FASEB J., 2000, 14(15):2383-6.
Meyer-Franke et al., "Astrocytes induce oligodendrocyte processes to align with and adhere to axons", Mol Cell Neurosci, 1999, 14(4-5), 385-97.
Milano et al., "Modulation of notch processing by g-secretase inhibitors causes intestinal goblet cell metaplasia and induction of genes known to specify gut secretory lineage differentiation", Toxicological Sciences, 2004, 82:341-358.
Minter; et al., "Inhibitors of gamma-secretase block in vivo and in vito T helper type 1 polarization by preventing Notch upregulation of Tbx21", Nature Immunology (2005), 6(7):680-688.
Pinnix et al., "A novel gamma-secretase assay based on detection of the putative C-terminal fragment-gamma of amyloid beta protein precursor", J. Biol. Chem, 2001, 276(1):481-7.
Popko, "Notch Signaling: A Rheostat Regulating Oligodendrocyte Differentiation", Developmental Cell (2003), 5(5):668-669.
Schneider, "Palmitoylation is a sorting determinant for transport to the myelin membrane", J Cell Sci, 2005, 118:2415-23.

(Continued)

*Primary Examiner* — Gregory S Emch
(74) *Attorney, Agent, or Firm* — Bozicevic, Field & Francis LLP; Elizabeth A. Alcamo

(57) ABSTRACT

Methods are provided for enhancing myelination. Myelination is enhanced by administration of agents that are inhibitors of γ-secretase. Methods of screening for pharmaceutically active compounds that enhance myelination, and for genes involved in myelination are also provided.

5 Claims, 6 Drawing Sheets

OTHER PUBLICATIONS

Schroeter et al., "A presenilin dimer at the core of the gamma-secretase enzyme: insights from parallel analysis of Notch 1 and APP proteolysis", Proc. Natl. Acad. Sci. USA, 2003, 100(22):13075-13080.

Seubert; et al., "Secretion of beta-amyloid precursor protein cleaved at the amino terminus of the beta-amyloid peptide", Nature (1993), 361:260-263.

Shearmen et al., "L-685,458, an aspartyl protease transition state mimic, is a potent inhibitor of amyloid beta-protein precursor gamma-secretase activity", Biochemistry, 2000, 39(30):8698-8704.

Stidworthy et al., "Notch1 and Jagged1 are expressed after CNS demyelination, but are not a major rate-determining factor during remyelination", Brain, 2004, 127(Pt 9):1928-41.

Takahashi et al., J. Biol. Chem., "Sulindac sulfide is a noncompetitive gamma-secretase inhibitor that preferentially reduces Abeta 42 generation", 2003, 278(20):18664-70.

Von Boehmer, "Notch in lymphopoiesis and T cell polarization", Nature Immunology (2005), 6(7):641-642.

Wang et al., "A role for the helix-loop-helix protein Id2 in the control of oligodendrocyte development", Neuron (2001), 29(3):603-14.

Wang; et al., "Notch Receptor Activation Inhibits Oligodendrocyte Differentiation", Neuron (1998), 21:63-75.

Wang; et al., "Up a Notch: Instructing Gliogenesis", Neuron (2000), 27:197-200.

Watkins; et al., "A New Co-Culture System of Purified Neurons and Oligodendrocytes for Examining CNS Myelination in vitro", Abstracts of the Annual Meeting of the Society for Neuroscience, Nov. 7, 2002, program No. 448.9.

Windrem et al., Nature Medicine, "Fetal and adult human oligodendrocyte progenitor cell isolates myelinate the congenitally dysmyelinated brain", 2004, 10(1):93-97.

Wolfe et al., "A substrate-based difluoro ketone selectively inhibits Alzheimer's gamma-secretase activity", J. Med. Chem. (1998), 41(1):6-9.

Wolfe, "gamma-Secretase Inhibitors as Molecular Probes of Presenilin Function", Journal of Molecular Neuroscience (2001), 17:199-204.

* cited by examiner

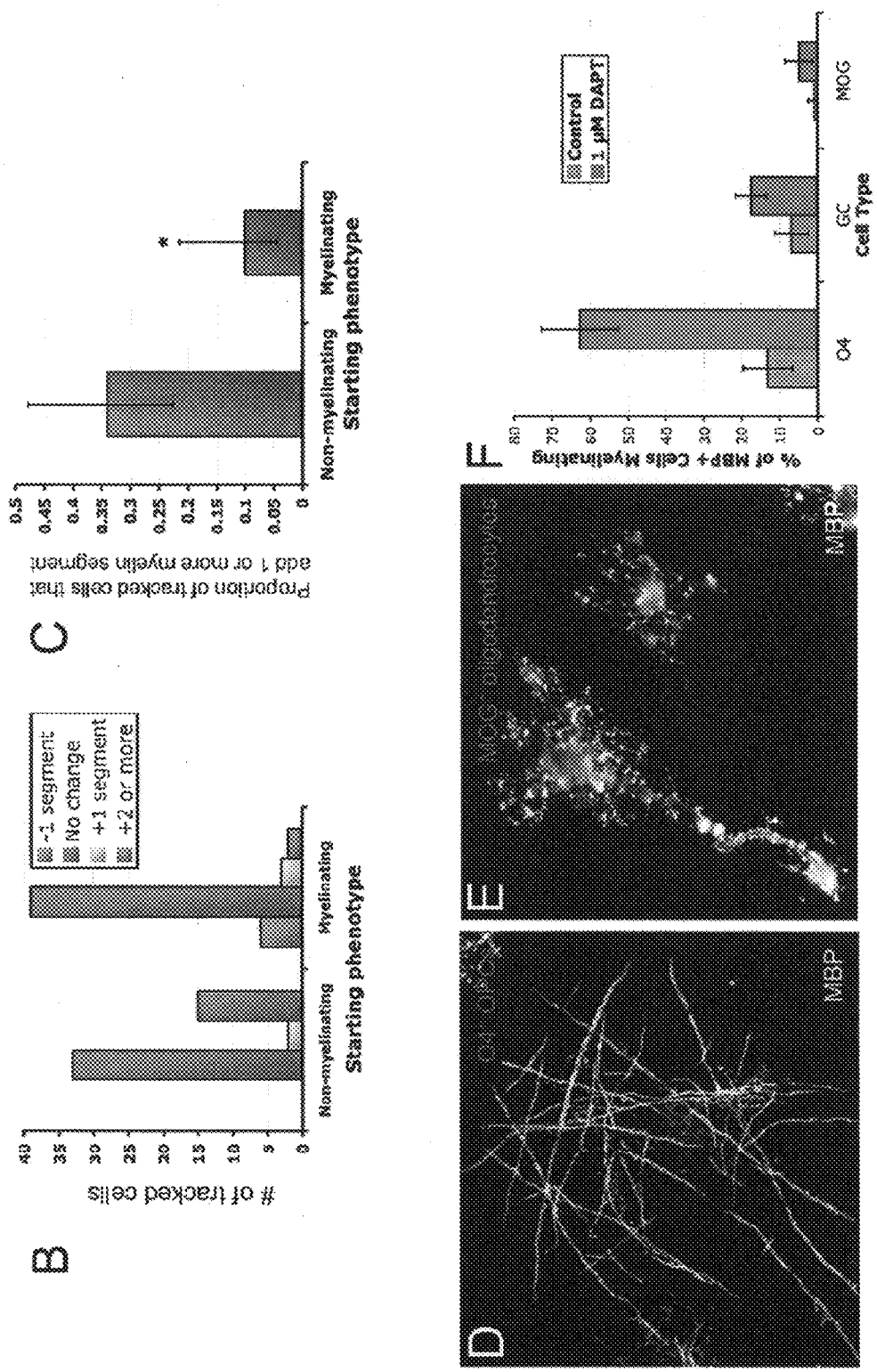

BLOCKADE OF GAMMA-SECRETASE ACTIVITY TO PROMOTE MYELINATION BY OLIGODENDROCYTES

This invention was made with Government support under contract EY010257 awarded by the National Eye Institute, NIH. The Government has certain rights in this invention.

Myelin is a vital component of the central and peripheral nervous system. The systematic wrapping of an axon by insulating myelin sheaths is a remarkable event in the development of the vertebrate central nervous system. Consisting of 70% lipid and 30% protein, myelin is formed both by oligodendrocytes (OLs) in the central nervous system (CNS) and by Schwann cells in the peripheral nervous system (PNS). Working as insulation, myelin enhances the speed and integrity of nerve signal propagation down the neural axon, allowing signals to pass back and forth between the brain and the nerves of the periphery over long distances. Damage to the myelin sheath can lead to a variety of neurological disorders with often devastating consequences.

Previous studies have shown that myelination is a multistep process in which a myelinating cell adheres to an axon, then ensheaths and wraps it, culminating with exclusion of the cytoplasm from the spiraling processes to form compact myelin. The myelin sheath is formed by the plasma membrane, or plasmalemma, of glial cells: oligodendrocytes in the CNS, Schwann cells in the PNS. The plasmalemma makes contact with the axon and then begins to wrap around it, spiral fashion, the inner mesaxon continuing to circle the axon as the plasmalemma grows and flattens, squeezing out most of the cytoplasm, until the end result is a laminated sheath consisting of multiple concentric lamellae formed of plasma membrane, each lamella consisting of a total of four lipid leaflets.

This process is aided by a variety of myelin specific proteins, whose synthesis is induced by the initiation of contact between the glial plasma membrane and the axon. This contact also leads to a strong increase in the rate of growth of the plasmalemma itself, necessary for the continued spiraling. The proteins assist by fusing the inner, cytoplasmic leaflets of the plasma membrane together, excluding the cytoplasm and compacting the layers; and by adhering the outer leaflet of the plasmalemma to the axon and to the outer leaflet on the apposed lamella, resulting in the proper flattened, multilayered myelin formation. Layers of the myelin sheath are connected by gap junctions, which simultaneously connect the layers and allow for communication between them, providing for nutrition and waste removal of even the innermost layers.

Myelin associated proteins include myelin basic protein, which is present on the inner leaflet of the plasma membrane, and appear to be involved in myelin compaction and maintaining the basic structure of the myelin sheath. Myelin associated glycoprotein is a single transmembrane-segment protein with a glycosylated extracellular domain, and a cell adhesion molecule. Proteolipid protein comprises the majority total protein in CNS myelin. PLP is a four-transmembrane-segment molecule comprising multiple long chains of fatty acids. Other proteins include P0; PMP22 and connexin 32, all of which are present in peripheral nervous system myelin, and are members of the immunoglobulin gene superfamily.

The myelin sheath is formed in segments along the length of the axon. Between segments are small unmyelinated areas known as the nodes of Ranvier. This arrangement allows for very fast neural impulse transmission via saltatory conduction, in which the active components of impulse propagation are concentrated in the nodes of Ranvier, while current flow within the axon takes place in the internodes. The integrity of the nerve conduction process can be assessed clinically through measurements of conduction velocity. When myelination fails at a particular region of axon, the spread of the action potential slows down or stops altogether, measured clinically as slowed conduction or conduction block, respectively.

Disorders of myelination can produce significant impairment in sensory, motor and other types of functioning when nerve signals reach their targets slowly, asynchronously, intermittently, or not at all. Disorders of myelination can be demyelinating, as a result of removal or degradation of myelin already formed; or dysmyelinating, as a result of deficient or defective myelin development or maintenance. These disorders can also be classified as hereditary or acquired. Many disorders affect both the CNS and the PNS. Included among the more common disorders of CNS myelination are multiple sclerosis, progressive multifocal leukoencephalopathy, optic neuritis, and Creutzfeld-Jakob disease.

Despite the importance of myelin for the rapid conduction of action potentials, little is known about the mechanism of myelination or the axon-glial signals that regulate the timing and location of myelination. One of the difficulties in studying myelination is the absence of good models. A general limitation of transgenic mice for studying the signals that control CNS myelination is that myelination occurs late in development. Transgenic mice deficient in particular molecules of interest such as neuregulin and Notch1 receptors often undergo embryonic lethality. Even in the case where lethality does not occur, perturbations in neuronal development may then indirectly alter myelination.

A robust culture system for studying CNS myelination would provide several experimental advantages. It would avoid the problem of embryonic lethality when testing candidate axonal signals by perturbing their levels selectively in either neurons or oligodendrocytes. It would also allow a clean dissection of whether and how particular axonal signals function in controlling particular stages of the oligodendrocyte lineage. Unfortunately, such in vitro studies have previously been limited by the lack of a robust culture system that permits rapid myelination. Although myelin is produced in co-cultures of neurons and Schwann cells, or oligodendrocytes, but with a significant delay before myelination occurs, which delay is not seen in vivo.

The present invention addresses means of enhancing myelination in vivo; and culture systems suitable for studying the myelination of neurons.

SUMMARY OF THE INVENTION

Compositions and methods are provided for enhancing myelination of neurons, particularly central nervous system neurons. Inhibiting the activity of γ-secretase is shown to significantly enhance the myelination of neurons by oligodendrocytes. Conditions that benefit from enhanced myelination include optic neuritis, multiple sclerosis, and other myelination disorders, which disorders may be a result of deficiencies in initial myelination, or of damage to myelination through inflammation, infection, trauma, toxicity, and the like.

Methods of enhancing myelination may include providing oligodendrocytes or precursors thereof, in combination with a γ-secretase inhibitor, to a site or sites of neurons requiring myelination. In other embodiments, pharmaceutical formulations of a γ-secretase inhibitor are administered locally or systemically to neurons requiring myelination.

In one embodiment of the invention, the inhibitor of γ-secretase is a pharmacologic inhibitor, e.g. a small organic compound. In another embodiment, the inhibitor as a genetic inhibitor, e.g. anti-sense oligonucleotide, siRNA, etc.

In another embodiment of the invention, culture models providing for rapid myelination of neurons are provided, which cultures find use in screening agents that may modulate myelination, in assays for cells and factors that affect myelination, and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
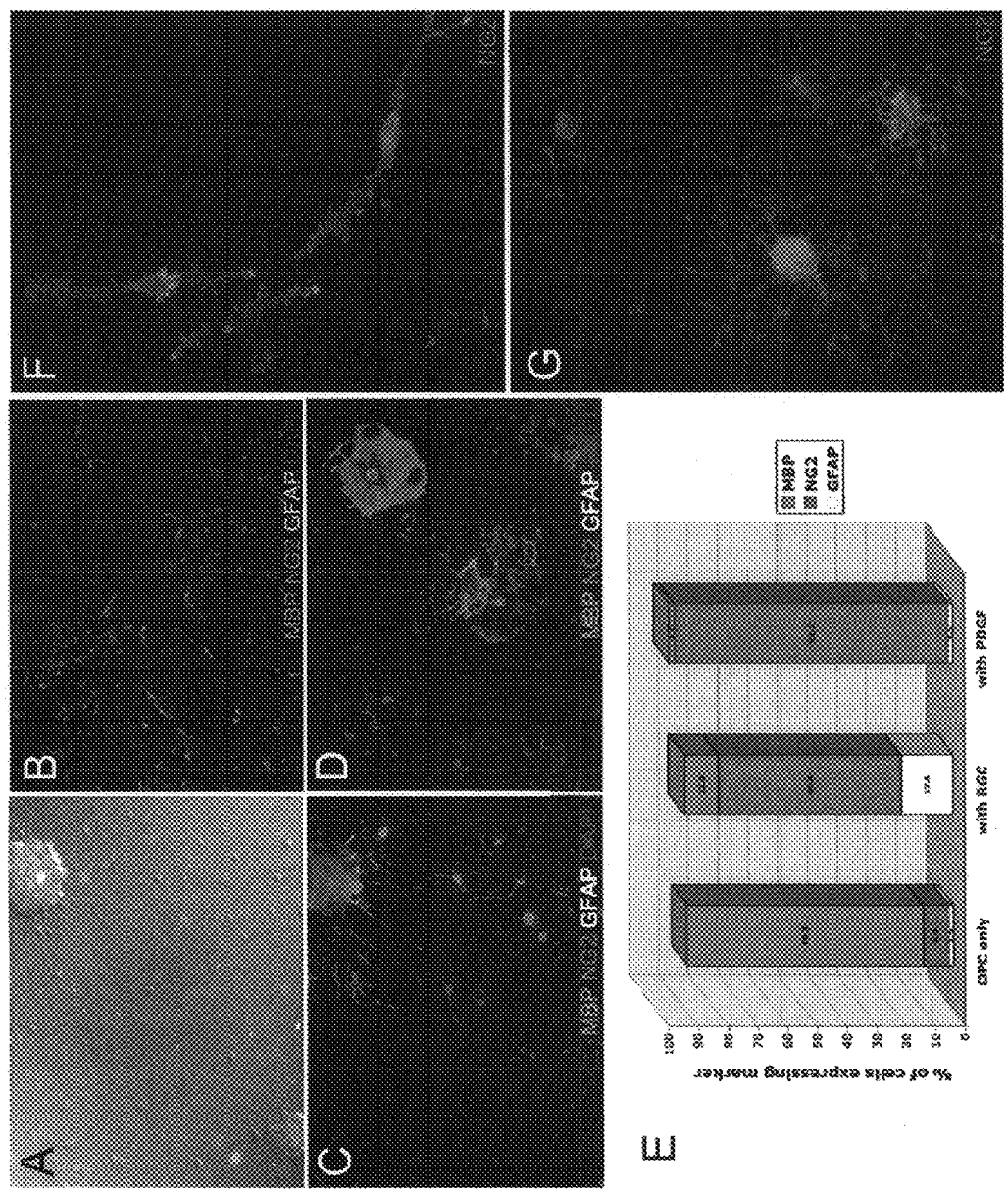
FIG. 1. Contact with RGC axons inhibits OPC differentiation. (A) Differential-interference contrast image of a coculture of OPCs with RGC reaggregates. (B-E) Immunolabeling of the field seen in (a) with markers for OPCs (NG2), oligodendrocytes (MBP), and astrocytes (GFAP) reveals strong effects of RGCs on OPC development (c) compared to the nearly uniform differentiation into oligodendrocytes of isolated OPCs (d) or the addition of 10 ng/ml PDGF (b). Quantitative evaluation indicates that RGCs inhibit OPC differentiation and promote differentiation into type 2-astrocytes in a significant number of OPCs (e). (F-G) RGCs induce a multipolar phenotype (g) in $NG2^+$ OPCs that is distinct from the bipolar morphology of rapidly dividing OPCs in PDGF (f).
Figure 2:
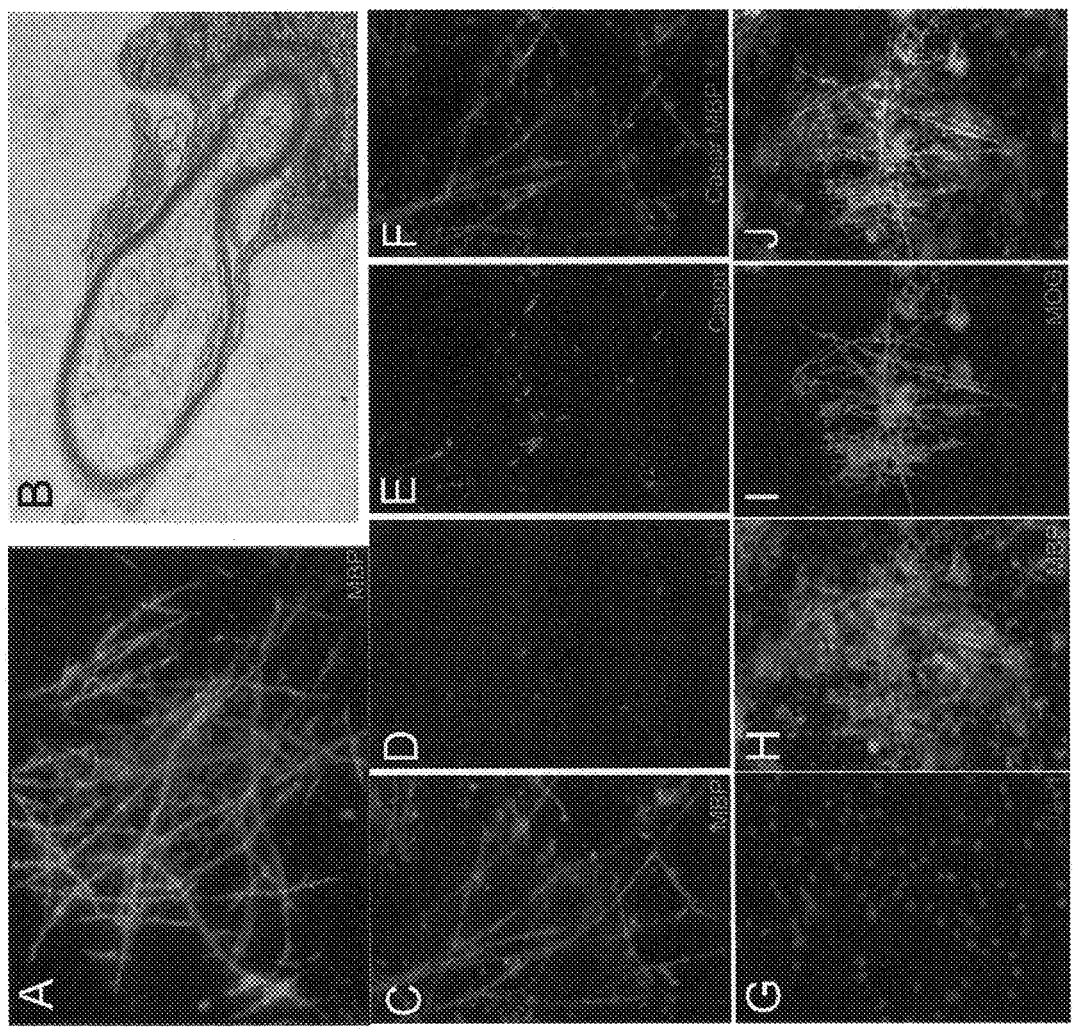
FIG. 2. Some oligodendrocytes form multiple mature myelin segments in OPC-RGC reaggregate cocultures. (A) An example of a myelinating oligodendrocyte immunostained with antibodies against MBP. (B) The presence of compact myelin is confirmed by electron microscopy. (C-F) Myelination in culture (c, MBP, green) induces specialization of axonal subdomains, such as sodium channel clustering at the node (d, pan-NaCh, blue) and Caspr clustering at the paranodes (e, Caspr, red). (G-J) Amongst a dense field of $MBP^+$ oligodendrocytes (g, DAPI, blue, and h, MBP, green), all of the myelin segments are formed by one $MOG^+$ oligodendrocyte (i, MOG, red).

Compositions and methods are provided for enhancing myelination of neurons, e.g. central nervous system neurons, by inhibiting the activity of γ-secretase in oligodendrocytes. The methods find use in vivo and in vitro, for example in the treatment of myelination disorders, in culture models for analysis of molecular mechanisms, genetic changes, etc., in drug screening, and the like.

The present invention provides new approaches to therapy for brain injury and disease, and provides compositions and methods effective to treat brain injury and disease. In particular, compositions and methods are provided for treating brain injury and disease, comprising administering γ-secretase inhibitors in a dose effective to restore myelination of axons in animals by oligodendrocytes, for example after injury to the brain, or as a therapy for demyelinating diseases, such as multiple sclerosis. In an animal in need of restored myelination due to neural injury or disease, a therapeutic amount of a γ-secretase inhibitor is administered, where the inhibitor may comprise a small molecule inhibitor, e.g. DAPT; etc.; or may comprise a genetic inhibitor, e.g. RNAi specific for γ-secretase, etc., in a dose effective to restore myelination of axons. The composition may be administered directly to the CNS, which route of administration can involve, for example, lateral cerebroventricular injection, focal injection, or a surgically inserted shunt into the lateral cerebroventricle of the brain of the patient.

In the method of restoring myelination of axons to an animal in need of restored myelination due to neural injury or disease, the neural injury or disease may comprise a disorder selected from the group consisting of trauma, toxin exposure, asphyxia or hypoxia-ischemia, perinatal hypoxic-ischemic injury, injury to or disease of the white matter of the central nervous system, acute brain injury, chronic neurodegenerative disease, and demyelinating diseases and disorders. In one embodiment of the invention, the chronic neurodegenerative disease is multiple sclerosis. In another embodiment, the demyelinating diseases and disorders comprise inflammatory involvement, including acute disseminated encephalomyelitis, optic neuritis, transverse myelitis, Devic's disease, the leucodystrophies; or non-inflammatory involvement, including progressive multifocal leukoencephalopathy, and central pontine myelinolysis.

The method of restoring myelination of axons in an animal in need of restored myelination may further comprise the administration of a therapeutically effective amount of oligodendrocytes, astrocytes, or progenitors thereof. In the treatment of myelination disorders associated with inflammation, agents useful in the inhibition of inflammation, e.g. β-interferon; anti-integrin specific antibodies, cytoxan, azathioprine, copaxone, naltrexone, prednisone, corticosteroids, and the like, may also be administered.

In another embodiment of the invention, a kit is provided, where the kit comprises a γ-secretase inhibitor formulated in a pharmaceutically acceptable buffer, a container for holding said γ-secretase inhibitor formulated in a pharmaceutically acceptable buffer, and instructions for administration. In a further aspect of the invention, the kit may further comprise a composition of myelin producing cells or progenitors thereof, e.g. fetal or adult oligodendrocyte progenitor cells (OPCs). These progenitor cells may be identified by their A2B5$^+$PSA$^-$NCAM$^-$ phenotype (positive for the early oligodendrocyte marker A2B5 and negative for the polysialylated neural cell adhesion molecule). Kits may further comprise therapeutic agents useful in the inhibition of inflammation, formulated in a pharmaceutically acceptable buffer.

Definitions

γ-Secretase. A multi-protein complex involved in proteolysis within the membrane, providing a proteolytic activity necessary for the production of beta-amyloid (Aβ), an amyloidogenic peptide linked to the pathogenesis of Alzheimer's disease. Active γ-secretase is a complex of four proteins, of which presenilin (PS) is thought to provide the active site through two highly-conserved aspartates, D257 and D385, located within transmembrane domains of the protein. To become active, immature PS must be processed and incorporated into a complex with other proteins to become stabilized. This includes a proteolytic cleavage by an enzyme termed "presenilinase" that produces N-terminal fragment and C-terminal fragments that remain associated with one another in the mature protease, with each fragment containing one of the two essential aspartates. Even this mature PS, however, is insufficient to cleave APP in the absence of the other members of the complex. These proteins, identified as nicastrin, Aph-1, and Pen-2, regulate maturation, stabilization and trafficking of the complex. Pen-2, for example, is required for the presenilinase cleavage of immature PS once it is incorporated into a complex with Aph-1 and nicastrin. Together, the complex of four proteins can reconstitute the γ-secretase activity, with PS alone sometimes itself referred to as "γ-secretase" based on its proposed role as the active core of the complex. As shown herein, postnatal acutely-isolated RGCs, OPCs, and OLs all express PS1 and PS2.

Integral membrane protein substrates for the regulated intramembrane proteolysis (RIP) activity of γ-secretase have been identified. The best-known of these substrates is Notch, whose biological activity depends both on its function as a cell surface receptor and a transcriptional regulator. Ligand-induced activation of Notch results in cleavage at the S2 site by proteases of the ADAM family, releasing the extracellular domain. The remaining truncated transmembrane form of Notch is them subject to cleavage at two sites within the membrane S3 and S4, the targets of γ-secretase. Notch ICD translocates to the nucleus where it interacts with the DNA-binding protein CBF1 and the Mastermind co-activator, triggering a switch from repression to activation of Notch target genes.

At least sixteen substrates of γ-secretase have been identified. Some of the identified targets of γ-secretase are ligands of receptors that are themselves known targets for γ-secretase, such as the Notch ligands Jagged and Delta, suggesting a role in "back-signaling" concurrent with receptor activation. In addition to Notch, other identified substrates of γ-secretase cleavage that are likely regulators of CNS myelination include N-cadherin, the cysteine-rich domain isoform of neuregulin-1 (CRD-NRG), and the neuregulin receptor erbB4.

The neuregulins (NRGs) are a large family of signaling proteins that includes multiple soluble and transmembrane isoforms encoded by at least four genes. Expressed by a variety of neurons, they may have complex, context-dependent effects on the development of myelinating glia), ranging from promoting proliferation of precursors to encouraging maturation of OLs. They are also likely to provide an axon-derived survival signal for developing OLs, perhaps in conjunction with integrin ligands such as laminin-2. They mediate these effects through transmembrane receptor tyrosine kinases of the erbB family, particularly heterodimers of erbB2/erbB3 and erbB2/erbB4. Although expressed in OLs, erbB3 seems to be dispensable in OL development.

γ-secretase inhibitors. A number of laboratories and commercial interests have developed specific inhibitors of γ-secretase activity. Among the most specific and effective described so far is N-[N-(3,5-Difluorophenacetyl-L-alanyl]-S-phenylglycine-t-butyl ester (DAPT), which inhibits both PS-1 and PS-2. This compound is an optimized derivative of a molecule that inhibited Aβ production in a screen of approximately 25,000 compounds. DAPT is a cell-permeable dipeptide non-transition state analog that can compete moderately for the γ-secretase active site in a displacement assay, suggesting some overlap between the binding site of DAPT and the active site.

Examples of γ-secretase inhibitors include:

| Compound | In cells | Cell-free | Displacement | Type |
|---|---|---|---|---|
| III-31-C | 0.2 μM | 10 μM | YES | Transition state |
| DAPT | 20 nM | 10 nM | YES | Non-transition state |
| Compound E | 0.3 nM | 3 nM | YES | Non-transition state |
| Isocoumarins | 80 μM | >200 μM | NO | Non-γ-secretase |
| | | | | JLK6 / JLK2 |
| D-Helical peptide 294 | 3 μM | 0.1 μM | NO | Substrate mimic |
| | | Boc-D-Val-Gly-Aib-D-Val-D-Val-D-He-Aib-D-Thr(OBn)-D-Val-Aib-OMe | | |
| Epoxide | 20 μM | 20 μM | YES Time-dependent | Irreversible |

| Compound | In cells | Cell-free | Displacement | Type |
|---|---|---|---|---|
| (Z-LL)$_2$-ketone, a SPP inhibitor | >100 μM | 30 μM | YES | Aspartyl protease inhibitor |

Peptidomimetic inhibitors include L-685,458 ((5S)-(t-Butoxycarbonylamino)-6-phenyl-(4R)hydroxy-(2R)benzyl-hexanoyl)-L-leu-L-phe-amide), described by Shearmen et al. (2000) *Biochemistry* 39, 8698-8704.

ALX-260-127 (also referred to as compound 11) is a reversible difluoro ketone peptidomimetic inhibitor of γ-secretase, described by Wolfe et al. (1998) J. Med. Chem. 41, 6.

Photoactivated gamma-secretase inhibitors directed to the active site of γ-secretase are described by Li et al. (2000) Nature 405(6787):689-94.

Sulindac sulfide (SSide) directly acts on gamma-secretase and preferentially inhibits the gamma(42)-secretase activity in an in vitro gamma-secretase assay using recombinant amyloid beta precursor protein C100 as a substrate, Takahashi et al. (2003) J Biol Chem. 278(20): 18664-70.

Various assays have also been described for screening γ-secretase inhibitors, for example by Takahashi et al., supra., an assay based on detection of the putative C-terminal fragment-gamma of APP by Pinnix et al. (2000) J Biol Chem. Oct 16.; cell free assays for γ-secretase activity by McLendon et al. (2000) FASEB J Oct 6

Other means of blocking or reducing γ-secretase activity include the introduction of genetic agents that directly inhibit the expression of presenilin, e.g. anti-sense oligonucleotides that hybridize to a portion of the presenilin transcript; and the like. Such methods also encompass the use of interference RNA (RNAi) technology. In this approach, a molecule of double-stranded RNA specific to a subunit of γ-secretase, e.g. presenilin, is used. RNAi technology refers to a process in which double-stranded RNA is introduced into cells, e.g. oligodendrocytes, expressing a subunit of γ-secretase to inhibit expression of the targeted gene, i.e., to "silence" its expression. The dsRNA is selected to have substantial identity with the targeted gene. In general such methods initially involve in vitro transcription of a nucleic acid molecule containing all or part of a targeted gene sequence into single-stranded RNAs. Both sense and anti-sense RNA strands are allowed to anneal under appropriate conditions to form dsRNA. The dsRNA is prepared to be substantially identical to at least a segment of a targeted gene. The resulting dsRNA is introduced into cells via various methods, thereby silencing expression of the targeted gene. Because only substantial sequence similarity between the targeted gene and the dsRNA is necessary, sequence variations between these two species arising from genetic mutations, evolutionary divergence and polymorphisms can be tolerated. Moreover, the dsRNA can include various modified or nucleotide analogs. Usually the dsRNA consists of two separate complementary RNA strands. However, in some instances, the dsRNA may be formed by a single strand of RNA that is self-complementary, such that the strand loops back upon itself to form a hairpin loop. Regardless of form; RNA duplex formation can occur inside or outside of a cell. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

Also within the scope of the invention are methods of inhibiting γ-secretase by expression of dominant-negative or familial Alzheimer's disease (FAD) mutants of presenilin-1 or presenilin-2 and the knockout/disruption of genes (or gene products) that are essential for γ-secretase activity, such as presenilin, nicastrin, Pen-2, or Aph-1.

Conditions of interest. Conditions of interest are disorders in which there is a lack of axon myelination. In some embodiments, the axons are CNS axons. Such conditions may include trauma, toxin exposure, asphyxia or hypoxia-ischernia, perinatal hypoxic-ischemic injury, injury to or disease of the white matter of the central nervous system, acute brain injury, Creutzfeld-Jakob disease, chronic neurodegenerative disease, and demyelinating diseases. Multiple sclerosis is of particular interest.

The demyelinating diseases and disorders may include acute disseminated encephalomyelitis, optic neuritis, transverse myelitis, Devic's disease, the leucodystrophies, progressive multifocal leukoencephalopathy, and central pontine myelinolysis.

Chronic demyelinating conditions may include chronic immune demyelinating polyneuropathy (CIDP); multifocal CIDP; multifocal motor neuropathy (MMN), anti-MAG syndrome; galop syndrome; anti-sulfatide antibody syndrome (with serum M-protein); anti-GM2 antibody syndrome; POEMS syndrome; perineuritis; IgM anti-GD1b antibody syndrome; and the like.

Multiple Sclerosis (MS) is the most common of CNS demyelinating diseases. Generally striking between the ages of 20 and 50 and more frequently in women than in men, the disease is believed to have both viral and autoimmune etiologies, as well as a genetic component. Pathologically, the hallmarks of MS are areas of white matter lesion known as plaques whose features include both perivascular inflammation and demyelination. These plaques can occur anywhere in the white matter, but are most frequently found in the optic nerves, brainstem, cerebellum and spinal cord; the location of the plaques often corresponds to the clinical symptoms observed. Plaque ultrastructure includes infiltration with macrophages or microglia and phagocytosis of myelin, degenerative changes in the myelin, separation of the outer lamellae of the myelin sheath, and preservation of the axon itself. The severity of the demyelination, and the possibility of remyelination, depends upon the condition of the oligodendrocytes. In early disease and/or in some patients, the plaques contain viable oligodendrocytes, making at least partial remyelination of the denuded axons a possibility.

In its most typical presentation, MS is characterized by episodes of neurological dysfunction followed by periods of partial or complete remission of symptoms. The symptoms (initial, relapses or exacerbations) can appear over a period ranging from a few hours to few weeks. Depending on the course and the particular subtype of the disease, symptoms will either persist, progress or slowly resolve over weeks or months, possibly to the point of complete remission. A relapsing-remitting pattern is the most common for this disease.

The presence of an autoimmune etiology for MS is demonstrated by laboratory values. Typically the cerebrospinal fluid (CSF) contains high levels of IgG antibodies, and electrophoresis demonstrates oligoclonal bands, an indication of excess or abnormal antibody produced by one or more clones of plasma cells (activated B lymphocytes); in addition, the CSF contains abnormal numbers of CD4+ lymphocytes (T cells). The CSF also displays high levels of tumor necrosis factor (TNF) and interferons, both of which are cytokines responsible for macrophage activation and other immune-regulatory functions. In the blood, MS patients show abnormally high levels of various interleukins, cytokines that enhance immune response (particularly B and T lymphocytes). The proposed mechanism for autoimmune destruction is that T cells become activated against myelin, enter the CNS, and mediate the subsequent damage that destroys the CNS myelin, either through phagocytosis of the myelin by macrophages or by apoptosis of the oligodendrocyte. The autoimmune antigenic targets in CNS myelin are most probably one or more of the myelin specific proteins.

For treatment of MS relapses, immunosuppression with corticotropin (ACTH) and corticosteroids (prednisone and methyl prednisone) is the standard approach to suppression of cell-mediated immunity and, to some degree, humoral immunity; the most important effect of this therapy is suppression of the inflammatory response. Recombinant beta-interferon has had good success in reducing the development of plaques over time. Other therapies include drugs that target the immune system, e.g. copolymer-1, T-cell receptor peptide immunization, anti-CD4 monoclonal antibody, azathioprine (Imuran), cyclophosphamide (Cytoxan), methotrexate, cladribine, intravenous immunoglobulin G); progesterone and simvastatin.

In the treatment of MS with the methods of the invention, there may be benefits to treating the immune dysfunction in combination with the present methods of enhancing myelination.

Progressive multifocal leukoencephalopathy (PML) is an opportunistic demyelinating infection characterized by progressive, virally-induced degradation of the subcortical oligodendrocytes, particularly in the parieto-occipital lobes. PML lesions begin as small patchy round or oval lesions which eventually coalesce to form increasingly large lesions. The lesions occur initially in the peripheral areas of the white matter, at the gray-white matter interface; later they may extend to the periventricular areas. This pattern distinguishes PML from MS, which is primarily periventricular; for example, lesions of the corpus callosum, which are common in MS, are relatively rare in PML. Brainstem, cerebellar and spinal cord lesions are found occasionally.

PML lesions generally spare the nerve cells, at least initially; they do not display an inflammatory character, although activated microglia and macrophages are present. The oligodendrocytes are enlarged, and contain huge eosinophilic intranuclear inclusions made up of viral particles. Another feature is abnormally large astrocytes of an almost neoplastic appearance, containing mitotic figures and multinucleated forms.

PML is an opportunistic infection affecting people primarily with AIDS, but it is also seen in the chronic leukemias, lymphoma, Hodgkin's disease, and renal transplant. It is caused by a ubiquitous,. usually nonpathogenic papovavirus known as the JC virus. PML is occasionally the first AIDS-defining condition in people with HIV infection, and accounts for as many as 4 percent of AIDS deaths. Most adults harbor the JC virus, usually in a peripheral site such as the kidneys, without any sign of infection; in immunocompromised individuals, by a mechanism that is incompletely understood, the virus replicates in the periphery and then migrates to the CNS to cause infection, possibly via infection of B lymphocytes.

Onset of PML is insidious, and may occur at any point in the progression of the underlying disease. Symptoms include weakness, apraxias (impaired skilled motor function), ataxia (gait problems), paralysis, blindness, mental deterioration, dementia, behavioral abnormalities, and occasionally seizures. There is no effective treatment, although research suggests that treatment of the underlying HIV disease via highly active antiretroviral therapy (HAART) may cause some regression of PML.

Central Pontine Myelinolysis (CPM) is characterized by demyelination of the white matter fibers in the central part of the basis pontis (anterior/basal pons), particularly attacking the corticospinal and corticobulbar tracts. It occurs occasionally as a complication of severe and prolonged hyponatremia, particularly when it is corrected too rapidly. CPM is also sometimes known as Osmotic Myelinolysis.

CPM is characterized by concentrated, frequently symmetric, noninflammatory demyelination within the central basis pontis that shows up clearly as hyperintense (bright white) regions on T-2 weighted MRI (hypointense on T-1). In at least 10% of patients with CPM, demyelination also occurs in the pontine tegmentum and in extrapontine regions including the midbrain, thalamus, basal nuclei, cerebellum and internal capsule. CPM occurs in patients with electrolyte disturbances, particularly hyponatremia, of any etiology (for example in liver transplant and burn patients), although its rarity suggests an additional risk factor which has not been determined. The lesions on MRI are very characteristic, showing an oval shape on sagittal images, a bat-wing configuration on coronal images and various shapes on the axial images.

The leukodystrophies are a group of inherited white matter diseases that result in dysmyelination in the central nervous system. Several of them affect the peripheral nervous system as well. These disorders generally have onsets in infancy or early childhood, although some have variants that manifest later in life. All of them cause severe neurological damage that is progressive and ultimately fatal; there is so far no cure, but in some cases treatments have been developed that improve functioning and extend lives. Compared with multiple sclerosis, the leukodystrophies cause similar symptoms, although usually at a much earlier age; however, there is no autoimmune or inflammatory component and the course tends to be monophasic (steadily progressive) rather than relapse-remitting as in MS. Most of the leukodystrophies are storage disorders, resulting in dysmyelination (improper myelination) and in some cases demyelination.

Demyelinating diseases of the peripheral nervous system include Guillain-Barre Syndrome (GBS); the most common acute neuromuscular paralytic syndrome. Characterized by weakness, parasthesia, hyporeflexia, and sometimes autonomic dysfunction, it may in severe cases lead to respiratory failure. Generally it is strictly demyelinating, although in subset of patients some axonal damage occurs. GBS usually strikes following some other significant medical event, most often an infection; it can occur at any age, and it is somewhat more common among men. GBS is generally agreed to be the result of autoimmune response triggered by one of a number of medical conditions. By far the most common trigger is bacterial or viral infection.

Chronic immune demyelinating polyneuropathy (CIDP) is a sporadic acquired polyneuropathy that presents with both proximal and distal weakness and impaired tendon reflexes in the extremities. In addition, sensory loss is usually present, most often with deficits to vibration and touch. The pathogenesis of this disease is presumed to be autoimmune, with evidence of both cell-mediated and humoral processes, but the mechanism is unknown. CIDP can occur at any age, and when seen in childhood may mimic an inherited neuropathy such as Charcot-Marie-Tooth disease. The disease is seen in all age groups. The initial symptom is a slowly progressive numbness and tingling that usually begins distally in the feet, and progresses proximally, followed by weakness that ascends in the same pattern. Tendon reflexes are reduced or absent early in the disease course in both arms and legs. As the sensory modalities become involved, balance and gait become affected. As the disease progresses, symptoms in the majority of patients include symmetrical motor and sensory involvement in both upper and lower extremities, including limb weakness that is almost as severe (or more so) in proximal as in distal muscles, but there is little muscle wasting. The onset of CIDP symptoms is usually gradual, approximately 35% have a progressive or monophasic course, while the majority (65%) have a relapse-remitting course; the latter is associated with a significantly earlier age of onset and greater cranial nerve involvement.

In the CSF, cytoalbuminologic dissociation and elevated myelin basic protein (MBP) levels indicate myelin breakdown. Nerve biopsy shows hypomyelination, segmental demyelination, and evidence of demyelination/remyelination cycles. Mononuclear infiltrates and macrophage-mediated myelin stripping similar to that found in GBS are sometimes visible. Nerve hypertrophy is often visible in MRI, especially in the cauda equina region of the spine.

Anti-MAG syndrome is also a chronic demyelinating polyneuropathy that has some similarities to both other acquired and hereditary neuropathies, especially Charcot-Marie-Tooth disease Type I. Its most striking distinguishing feature is the fact that in all patients there is an IgM antibody to MAG protein, a glycoprotein specific to myelin. Anti-MAG symptoms include symmetric, primarily sensory loss in the distal limbs, first in the legs and later in the arms. As the disease progresses, motor involvement, particularly weakness, follows in the same in the same symmetric, primarily distal lower limb pattern. In the more severe cases, gait disorder and intention tremor may occur, particularly in the arms, will occur. Involvement of sensory systems is at all times greater than motor, distal greater than proximal, and lower limbs greater than upper.

Therapeutic Methods

As indicated above, the present invention is based upon the surprising finding that gamma secretase inhibitors are capable of promoting myelin production. This stimulation of myelin production is achieved through inhibiting the effective concentration or amount of γ-secretase in the nervous system of a patient, usually the CNS.

The compositions and methods of the invention find use in the treatment of mammals, such as human patients, suffering from neural injury or disease. Still more generally, the compositions and methods of the invention find use in the enhancement of myelin production following insult in the form of trauma, toxin exposure, asphyxia or hypoxia-ischemia; or from chronic neural injury or neurodegenerative disease, such as multiple sclerosis (MS); or from other demyelinating diseases and disorders. Patients suffering from such diseases or injuries will benefit greatly by a treatment protocol able to initiate remyelination.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

An effective dose is the dose that, when administered for a suitable period of time, usually at least about one week, and may be about two weeks, or more,.up to a period of about 4 weeks, 8 weeks, or longer will evidence an increase in the myelination of targeted cells. It will be understood by those of skill in the art that an initial dose may be administered for such periods of time, followed by maintenance doses, which, in some cases, will be at a reduced dosage.

The compounds can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

For some conditions, particularly central nervous system conditions, it may be necessary to formulate agents to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic or imaging compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

The calculation of the effective amount of compounds to be administered is within the skill of one of ordinary skill in the art, and will be routine to those persons skilled in the art. Needless to say, the final amount to be administered will be dependent upon the route of administration and upon the nature of the neurological disorder or condition that is to be treated.

For inclusion in a medicament, γ-secretase inhibitors may be obtained from a suitable commercial source. As a general proposition, the total pharmaceutically effective amount of the γ-secretase inhibitor compound administered parenterally per dose will be in a range that can be measured by a dose response curve.

A γ-secretase inhibitor to be used for therapeutic administration must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The γ-secretase inhibitor ordinarily will be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will be different from patient to patient. A competent clinician will be able to determine an effective amount of a therapeutic agent to administer to a patient to enhance myelination. Utilizing $LD_{50}$ animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Mammalian species that may be treated with the present methods include canines and felines; equines; bovines; ovines; etc. and primates, particularly humans. Animal models, particularly small mammals, e.g. murine, lagomorpha, etc. may be used for experimental investigations. Other uses include investigations where it is desirable to investigate a specific effect in the absence of T cell mediated inflammation.

The methods of the present invention also find use in combined therapies. A number of agents may be useful in the treatment of MS, including beta-interferons, glatiramer acetate, naltrexone, tysabri, corticosteroids, etc. The combined use of, for example, immunomodulatory agents and myelinating enhancers may have the advantages that the required dosages for the individual drugs is lower, and the effect of the different drugs complementary.

Methods may further comprise administering a composition of myelin producing cells or progenitors thereof, e.g. fetal or adult oligodendrocyte progenitor cells (OPCs). These progenitor cells may be identified by their A2B5$^+$PSA$^-$NCAM$^-$ phenotype (positive for the early oligodendrocyte marker A2B5 and negative for the polysialylated neural cell adhesion molecule).

In Vitro Culture Systems

In one embodiment of the invention, tissue culture systems are provided in which axons are myelinated in a physiologically normal time frame. Previous attempts to induce myelination within these parameters have been unsuccessful. This failure of myelination was due, in part, to the arrangement of axons in the previous culture setup. Dissociated neurons extend axons and dendrites in a complex meshwork. These conditions, however, bear little resemblance to the developing nerve, where oligodendrocyte progenitor cells develop amongst a dense array of axons, in the absence of neuronal cell bodies and dendrites. The co-culture system of the present invention provides conditions mimics this in vivo arrangement. The coculture system of the invention is useful for examining crucial axon-glial interactions that regulate myelination distinct from factors that simply influence the differentiation of purified OPCs.

Acutely-purified neurons, e.g. retinal ganglion cells, dorsal root ganglion cells, etc., are plated at high density on a non-adhesive substrate for a period of time sufficient for reaggregation, usually from about one, two three or more days. During this time, the neurons adhere to one another in reaggregates of tens to hundreds of cells. These reaggregates are then collected and plated on protein, e.g. laminin, etc. coated coverslips, after which they rapidly extend dense beds of axons radially. Few dendrites extend from these reaggregates. Under these conditions, neuronal cell bodies and dendrites are spatially restricted, creating multiple regions of dense axon beds. Acutely-purified oligodendrocyte progenitor cells (OPC) are added after a period of time sufficient for axon formation, usually about one week. After addition of the OPC, myelin segments can be observed by MBP immunostaining or electron microscopy within as little as seven days in culture. However, although the co-culture is permissive for myelination, the majority of MBP-expressing OLs still fail to myelinate the many adjacent axons.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. The specific culture conditions are chosen to achieve a particular purpose, i.e. maintenance of progenitor cell activity, etc.

In some embodiments of the invention, the co-cultures are grown in the absence of trophic factors that are conventionally used to support their long-term survival of neurons and oligodendrocytes in culture. Typical cultures contain, in addition to other factors, CNTF and forskolin. In the cultures of the present invention, the trophic support between neuron and oligodendrocyte provide sufficient factors to allow the removal of these exogenously added trophic factors, thus minimizing interfering effects of exogenous factors.

The subject co-cultured cells may be used in a variety of ways. For example, the nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions that promote myelination.

Expression Assays

In one embodiment of the invention, the tissue culture system is used to examine gene expression in myelinating cells. The expressed set of genes may be compared with a variety of cells of interest, e.g. in the absence and presence of γ-secretase inhibitors; in comparison with cultures lacking dense axon beds; in the absence or presence of oligodendrocytes; etc. For example, one can perform experiments to determine the genes that are regulated during myelination.

Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A$^+$ mRNA. One of skill in the art can readily use these methods. to determine differences in the size or amount of mRNA transcripts between two samples. For example, the level of particular mRNAs in progenitor cells is compared with the expression of the mRNAs in a reference sample, e.g. hepatocytes, or other differentiated cells.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., Science (1995) 270:484). SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific polynucleotide sequences (or restriction enzyme sites) are used as unique identifiers of genes, coupled with information about fragment length or fragment location within the expressed gene. The relative representation of an expressed gene with in a sample can then be estimated based on the relative representation of the fragment associated with that gene within the pool of all possible fragments. Methods and compositions for carrying out DD are well known in the art, see, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an arrays are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In another screening method, the test sample is assayed at the protein level. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods of qualitative or quantitative detection of levels or amounts of differentially expressed polypeptide can be used, for example ELISA, western blot, immunoprecipitation, radioimmunoassay, etc.

Screening Assays

The culture system described herein provides a useful system to screen candidate agents for activity in modulating myelination. To that end, it has been shown that γ-secretase inhibitors have a potent effect on enhancing myelination. Addition of a γ-secretase inhibitor strongly increases the number of myelin segments detected by MBP and MOG staining. Myelin segments can be observed in as little as three days after plating acutely-purified OPCs, with a large number of myelinating OLs observed by six days in culture. Normal paranodal and nodal differentiation is also observed in these cultures by immunostaining. Agents can also be screened for an effect on the inhibition of myelination, e.g. by adding a candidate agent to the culture system in the presence of a γ-secretase inhibitor.

In screening assays for biologically active agents, cells, usually cocultures of cells as described above, are contacted with the agent of interest, and the effect of the agent assessed by monitoring output parameters, such as extent of myelination, expression of markers, cell viability, and the like.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992):

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81).

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

γ-Secretase activity in CNS Myelination

In order to observe myelination by time lapse microscopy, we first developed a rapidly myelinating CNS co-culture system. We took advantage of established protocols to purify and culture rat retinal ganglion cells (RGCs), whose axons form the optic nerve, in the absence of glia. Whereas nearly all CNS neurons require glia for long-term survival in culture, dissociated RGCs can be purified by immunopanning and grown in defined medium for weeks, during which time they extend extensive networks of axons and dendrites on a laminin substrate. These networks, however, may not be suitable for the analysis of interactions of axon bundles with glia in developing CNS tracts.

We therefore adapted these protocols to produce cultures in which isolated oligodendrocyte precursor cells (OPCs) can interact specifically with multiple CNS axons. Purified RGCs were allowed to reaggregate into clumps of tens to hundreds of neurons prior to plating on an adhesive laminin-coated surface. These RGC reaggregates then extend dense beds of axons radially (with few dendrites, which almost exclusively grow within the reaggregate). After 10-14 days, these axons serve as a substrate for the seeding of purified OPCs. As shown in FIG. 1A, each OPC in this coculture system contacts multiple axons, similar to its environment in the developing optic nerve, with analysis of interactions unencumbered by rapid proliferation or the presence of other optic nerve cells.

To investigate how contact with CNS axons affects the development of the oligodendrocyte lineage, we plated acutely purified OPCs either on substrate-coated glass coverslips or on RGC reaggregate cultures and evaluated their cell fate decisions three days later by triple-immunostaining for phenotypic markers of OPCs (the chondroitan sulfate proteoglycan NG2), oligodendrocytes (myelin basic protein, MBP), and astrocytes (glial fibrillary acidic protein, GFAP). As expected, in the absence of RGCs or the mitogen PDGF, nearly 80% of the cells differentiated into oligodendrocytes that express MBP by the third day of culture (FIGS. 1D & 1E), whereas the addition of PDGF caused the OPCs to proliferate rapidly (not shown) and to maintain a simple bipolar morphology (FIGS. 1B & 1E). Contact with RGC axons, however, dramatically altered the fate decisions made by the OPCs. Instead of differentiating almost exclusively into MBP-expressing oligodendrocytes, the majority of these cells (61±10%) remained NG2-positive, with a significant portion (17±4%) differentiating into type 2-astrocytes (FIGS. 1C & 1E). Interestingly, this inhibition of OPC differentiation was not a simple consequence of release of PDGF or other soluble mitogens by RGCs, as the axonal effect was contact-mediated. Moreover, these cells changed markedly from the bipolar shape characteristic of rapidly-dividing and migrating young OPCs (FIG. 1F) to the complex multipolar morphology (FIG. 1G) reminiscent of adult OPCs. These data indicate that developing CNS axons inhibit the differentiation of OPCs into oligodendrocytes.

We next evaluated whether the oligodendrocytes that do develop in these cocultures wrap axons to form compact myelin and mature axonal subdomains. Although previous cocultures of dissociated (unreaggregated) RGCs with OPCs had not resulted in any myelination at all, the current coculture of established RGC reaggregates with OPCs did result in clear examples of smooth tubes of MBP-positive myelin in as few as three days after the seeding of OPCs (FIG. 1A). The presence of compact myelin in the OPC-RGC reaggregate cocultures was confirmed by.electron microscopy (FIG. 1B). Moreover, when myelin did form, it was capable of inducing specialization within the axons, including nodal clustering of sodium channels and paranodal clustering of contactin-associated protein, or Caspr (FIGS. 1C-1F). Thus normal myelination and nodal differentiation occurs rapidly in this co-culture system.

Only a small portion of MBP$^+$ cells was associated with smooth tubes of myelin. Typically, less than 20% of the oligodendrocytes had associated myelin segments, and the majority failed to even align with axons, often producing a morphology nearly indistinguishable from those that develop in the absence of axons. We noted, however, that the oligodendrocytes that did myelinate rarely myelinated just one or two axonal segments, even when many nearby mature oligodendrocytes failed to myelinate at all. Even within a dense region containing many axons and MBP$^+$ oligodendrocytes, where each oligodendrocyte had an equal opportunity to interact with the same set of axons, all of the myelin segments were produced by just one or a few oligodendrocytes (FIG. 2G-2J). This observation suggests that the formation of myelin did not depend solely on contact of a mature oligodendrocyte process with a receptive axon but also on which of the mature oligodendrocytes had made the transition to a myelination-competent stage.

Figure 5:
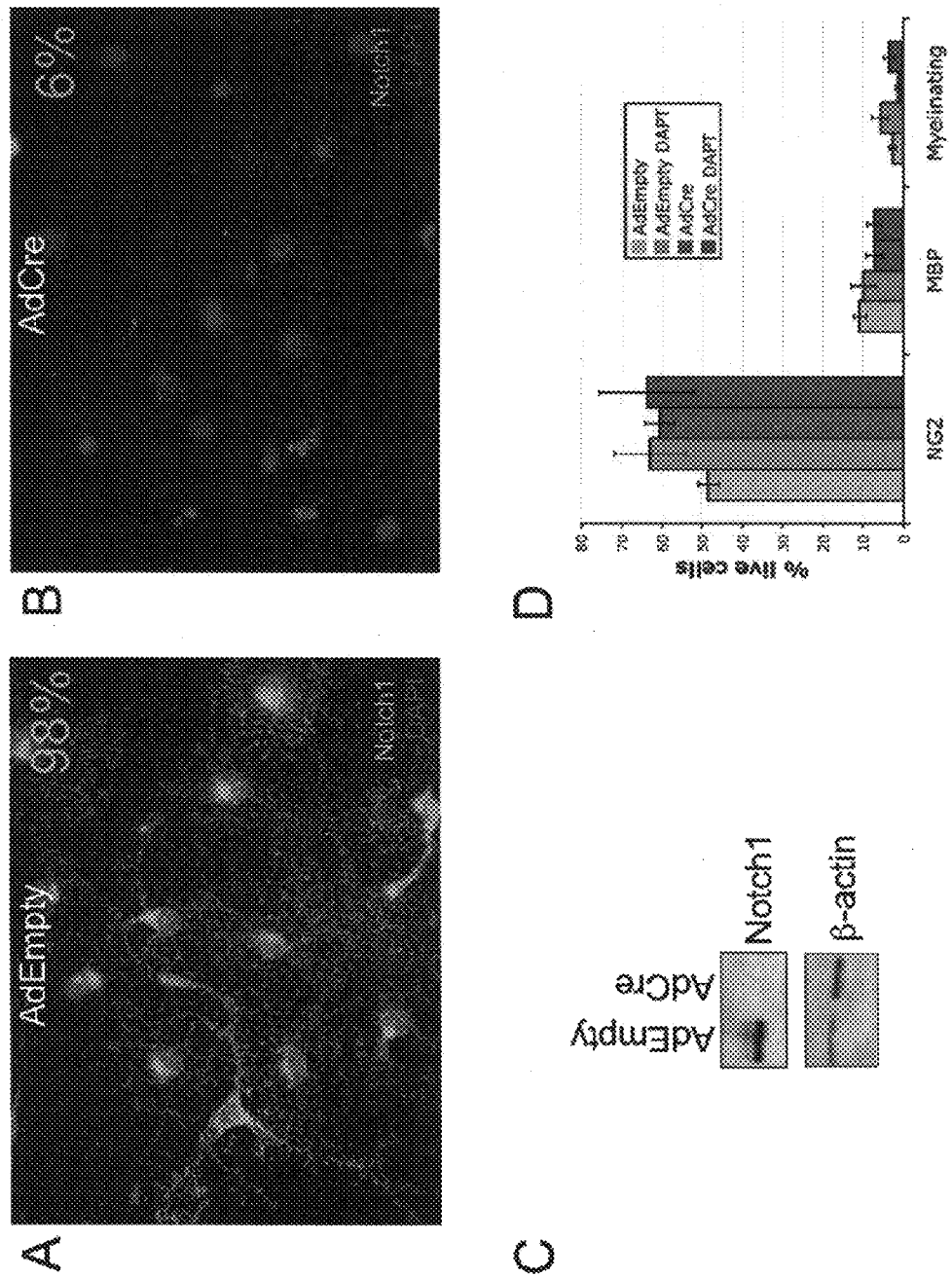
FIG. 5. Notch1 does not mediate the effects of γ-secretase inhibition on myelination. (A-C) Infection of OPCs from floxxed Notch1 mice ($Notch1^{f/f}$) with a recombinant adenovirus for expression of Cre recombinase (AdCre) results in rapid reduction of Notch1 protein. $Notch1^{f/f}$-OPCs, purified by immunopanning with anti-PDGFRα, were cultured for 2 days prior to infection for 24 hours with AdCre or a control virus (AdEmpty) at a multiplicity of infection of 10. The next day, cells were re-plated on RGC reaggregate cultures and on coverslips for analysis of Notch1 knockout, which was assessed by immunostaining (a,b) and Western blot analysis 24 hours later (c). (D) The γ-secretase inhibitor DAPT (1 μM) enhances myelination either in the presence (AdEmpty) or absence (AdCre) of glial Notch1, and knockout of Notch1 does not increase the proportion of cells that myelinate after six days of coculture with RGC reaggregates (n=5 coverslips/condition, 12 fields/coverslip).

Previous work had identified Notch1 signaling as a potential regulator of myelination by inhibiting differentiation of OPCs. To test whether activation of Notch1 by axonal Notch ligands is responsible for the large numbers of OPCs that failed to differentiate in the co-cultures, we added a potent inhibitor of Notch signaling to the cocultures. This drug, DAPT, inhibits the ligand-induced cleavage of Notch receptors (and many other substrates) by inhibiting the intramembrane protease γ-secretase, thus preventing the translocation of the Notch intracellular domain to the nucleus, where it affects transcription of target genes. Addition of DAPT did not consistently alter the proportion of NG2$^+$ OPCs or MBP$^+$ oligodendrocytes in these cocultures significantly (FIG. 3C), indicating that Notch1 signaling is not primarily responsible for the axonal inhibition of OPC differentiation. Similarly, Cre recombinase-mediated conditional knockout of Notch1 in mouse OPCs also did not alter the proportions of OPCs and oligodendrocytes in these RGC containing cocultures (FIG. 5).

Regardless of the presence or absence of Notch1, however, DAPT (1 µM) had an unanticipated effect. Its addition to co-cultures significantly increased the proportion of MBP$^+$ oligodendrocytes that formed myelin segments (FIG. 3A-3C), demonstrating a role for γ-secretase activity in the regulation of myelination. These data indicate that γ-secretase, acting on an unknown substrate, regulates the transition of MBP+ oligodendrocytes to a myelination-competent stage.

Figure 3:
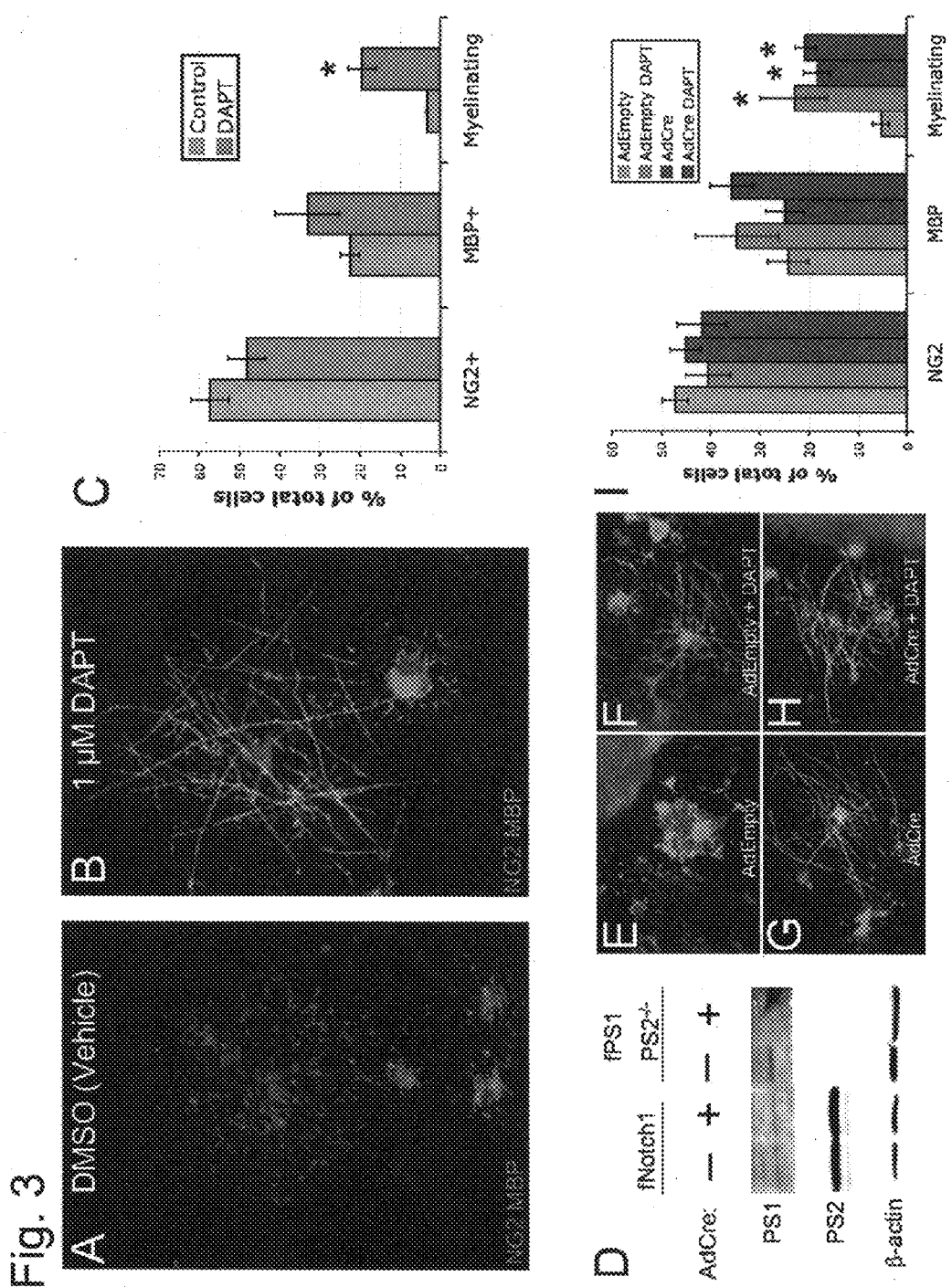
FIG. 3. Inhibition of glial γ-secretase activity promotes the transition to a myelinating oligodendrocyte. (A) In six-day-old cocultures stained with antibodies against MBP (green) and NG2 (red), the majority of $MBP^+$ oligodendrocytes fail to wrap axons. (B) In the presence of 1 μM DAPT, however, the majority of oligodendrocytes myelinate. (C) Quantification of cell fates reveals that the predominant effect of γ-secretase inhibition is to increase the proportion of $MBP^+$ oligodendrocytes that myelinate (n=3 coverslips/condition; 10 fields/coverslip; mean±standard deviation; *p<0.005, unpaired t-test). (D) Infection of OPCs purified from presenilin conditional double knockout (cDKO) mice with an adenovirus that directs expression of Cre recombinase (AdCre) results in loss of presenilin-1 protein within 1 day of plating on RGCs. Western blots of OPCs infected with AdCre or a control virus (AdEmpty) were probed for presenilin-1 and presenilin-2. OPCs from conditional Notch1 mice were used as a control, and β-actin was probed to ensure equal loading. (E-H) Cocultures of presenilin cDKO OPCs with RGC reaggregates were stained after 6 days with anti-MBP (green) and anti-NG2 (red) to determine the fates of the AdEmpty—(e,t) and AdCre-infected (g,h) OPCs in the presence (f,h) or absence (e,g) of 1 μM DAPT. (I) Quantification of cell fates reveals that knockout of glial presenilin-1 by infection with AdCre promotes myelination to a level comparable with addition of 1 μm DAPT (n=5-6 coverslips/condition; 8 fields/coverslip; mean±standard deviation; *p<0.001, compared to AdEmpty control by one-way ANOVA with post-hoc Tukey-Kramer multiple comparisons test).

To determine whether glial or neuronal γ-secretase was responsible for the observed regulation of myelination, we isolated OPCs from transgenic mice that lose an essential component of the γ-secretase complex, presenilin-1, upon Cre-mediated recombination. To avoid compensatory effects, these mice are also null for the related presenilin-2 gene (FIG. 3D). These double conditional knockout OPCs, when infected with an adenovirus that directs expression of the Cre recombinase, show an enhancement in their propensity to become myelinating oligodendrocytes, equivalent to that seen upon addition of DAPT (FIG. 3E-I). These results demonstrate that disruption of the essential γ-secretase components presenilin-1 and -2 in glial cells is sufficient to enhance myelination of wildtype neurons.

Figure 4:
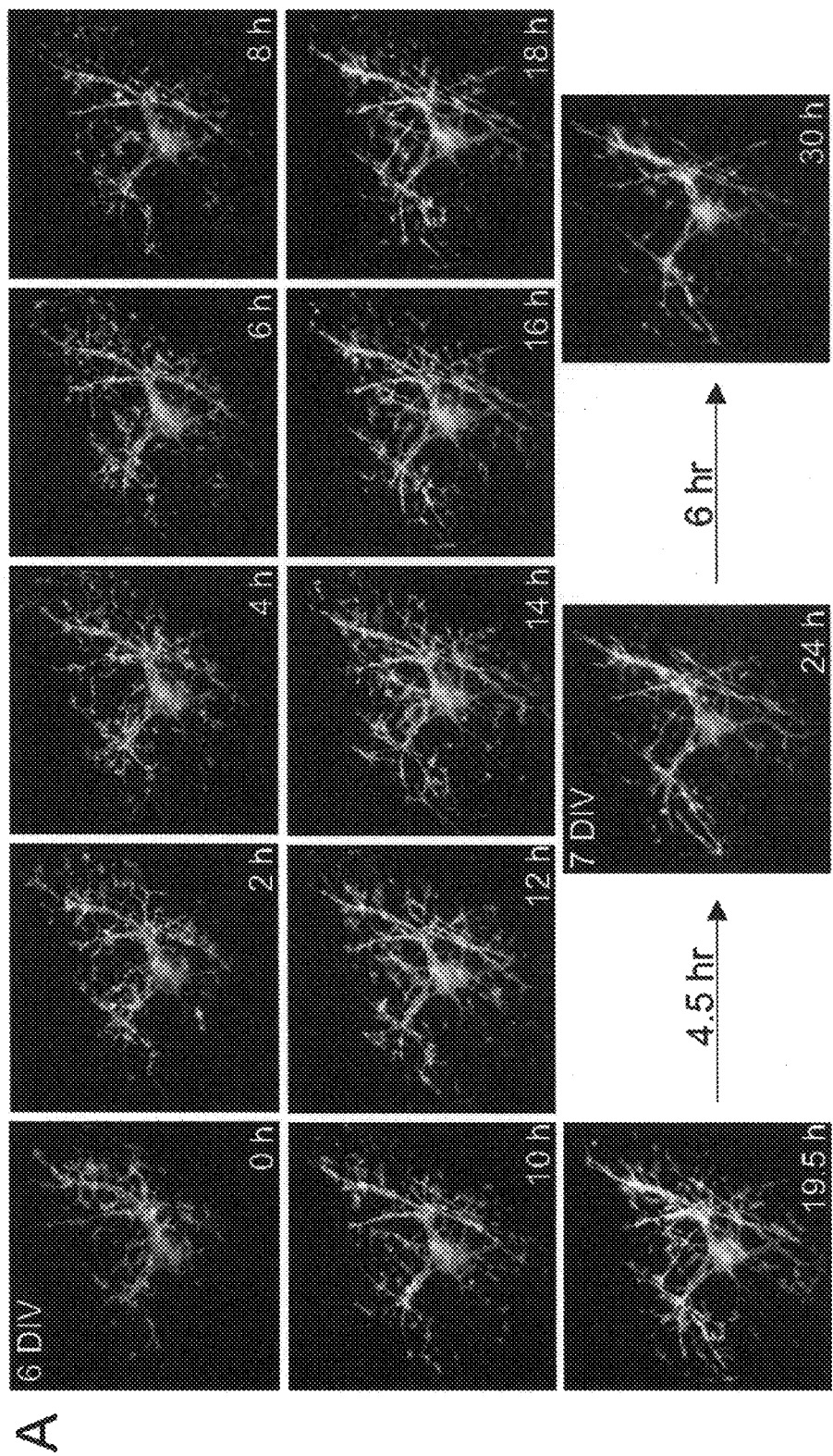
FIG. 4. All myelin segments are initiated by an oligodendrocyte within a brief period of time, and oligodendrocytes that have myelinated fail to form new segments. (A) Time-lapse microscopy reveals a sharp transition to a myelinating oligodendrocyte in OPC-RGC reaggregate cocultures. OPCs were transfected with a membrane-targeted form of EGFP and seeded onto established RGC reaggregate cultures. After 5 days of coculture (DIV), DAPT was added to a final concentration of 1 μM. One day later, the cell was imaged every 10 minutes at 37° C. during the transition to a myelinating oligodendrocyte. All the myelin segments were initiated within a brief window of between 4-16 hours after the beginning of imaging. Importantly, instead of establishing new myelin segments on the remaining naked axons, the non-myelinating processes became less active or retracted over the following 14 h. (B) Oligodendrocytes that have myelinated show a diminished capacity to initiate myelination when tracked over periods of 18-24 hours. (C) The proportion of tracked oligodendrocytes that initiate new segments (error bars=95% confidence interval, p<0.005 by z-test for comparing independent proportions). (D-F) Acutely-purified mature oligodendrocytes have a dramatically reduced capacity to form myelin segments. Acutely-purified P13 mouse $O4^+GalC^-$ OPCs, $GalC^+MOG^-PDGFR\alpha^-$ newly formed oligodendrocytes, and $MOG^+ PDGFR\alpha^-$ mature oligodendrocytes were plated on RGC reaggregates and co-cultured for 6 days in the presence or absence of 1 μM DAPT, prior to immunostaining with anti-MBP. The proportion of MBP-expressing cells that formed myelin was counted blindly (n=4 coverslips/condition; 8 fields/coverslip).

We next performed time lapse imaging in order to more directly evaluate whether a distinct stage of myelination could be observed in oligodendrocytes. We transfected OPCs with a farnesylated membrane-targeted variant of the enhanced green fluorescent protein, EGFP-F, and seeded them onto established RGC reaggregate cultures. Following a period of coculture of 3-7 days, during which time some of the OPCs differentiated into oligodendrocytes, we tracked 100 oligodendrocytes individually over periods of 20-24 hours, often following cells for an additional day, adding DAPT to maximize the chance that the tracked cell would myelinate within the narrow timeframe of observation. The oligodendrocyte seen in FIG. 4A illustrates our primary finding with those cells that did myelinate. Despite being in culture for six days prior to imaging, the cell had not yet initiated any myelin segments. After approximately six hours of imaging, the cell began producing multiple smooth tubes of membrane reminiscent of myelin, establishing as many as seven segments roughly concurrently over the next ten hours. We observed a qualitatively identical process in the majority of cells that we watched myelinate (FIG. 4). These data reveal that myelination by an oligodendrocyte is not simply a collection of serial events involving local interactions of individual processes with axon segments but is, in large part, a sharp, regulated transition to a distinct myelination-competent stage in which all of the processes that are destined to myelinate initiate myelination concurrently.

Interestingly, after this myelination period, the cell shown in FIG. 4A initiated no new segments over the following 14 hours, despite the presence of both unmyelinated axons nearby and non-myelinating oligodendrocyte processes. This stability was repeatedly observed when we initiated imaging of a cell that already had formed myelin segments, even if these segments were short or there were more processes aligned with axons that seemed poised to myelinate. Indeed, only 5 of the 50 observed oligodendrocytes that were already myelinating initiated new myelin segments during the period of observation (compared to 15 of the 50 cells that began as non-myelinating oligodendrocytes; p<0.005), indicating a dramatically reduced capacity to myelinate (FIG. 4B-4C). These findings reveal a brief window of time during an oligodendrocyte's development when it is capable of rapidly and robustly forming myelin. Consistent with this observation, we found that mature myelinating oligodendrocytes, acutely-purified from P13 mouse brain by immunopanning with anti-MOG antibodies following negative selection with anti-PDGFRα and A2B5 antibodies to remove OPCs and newly formed oligodendrocytes, largely failed to myelinate RGC axons in culture (FIG. 4D-4F). Even newly formed oligodendrocytes, those purified by positive selection for the early oligodendrocyte marker GalC following negative selection against MOG and OPC markers, have a reduced capacity to myelinate compared to O4$^+$GalC$^-$ OPCs (FIG. 4F). Therefore the transition to a myelination-competent stage seems to be followed by differentiation to a stable state in which the cell is refractory to the initiation of new myelin segments.

Taken together our findings provide evidence that myelination is an all-or-none process in which an oligodendrocyte forms most of its myelin segments concurrently during a limited window of time in its maturation. The likelihood that a given oligodendrocyte will decide to myelinate is greatly enhanced by inhibition of γ-secretase activity. Since the intracellular domains of many cleaved γ-secretase substrates serve to modulate transcription and likely therefore the characteristics of the entire cell, our findings suggest the existence of a nuclear-controlled myelination program that is inhibited prior to myelination by tonic γ-secretase activation.

A decision to myelinate may normally be triggered by γ-secretase inhibition when a sufficient number of an oligodendrocytes processes contact axons. The finding that developing oligodendrocytes exhibit a "critical period" in their maturation when they are able to myelinate has important implications for understanding why the CNS fails to remyelinate in demyelinating diseases such as Multiple Sclerosis (MS). Our findings help explain the previous observation that some cells in MS plaques express myelin proteins but fail to remyelinate and call attention to the importance of therapeutic strategies that promote the delivery or generation of new OPCs in demyelinated lesions. By greatly enhancing the ability of newly-formed oligodendrocytes to myelinate, γ-secretase inhibitors have the potential to enhance remyelination in MS.

In additional experiments, it has been shown that gamma secretase inhibition with DAPT profoundly enhanced myelination of dorsal root ganglion (DRG) neurons by oligodendrocytes, generalizing the importance of gamma secretase inhibitors in promoting CNS myelination.

Methods

Purification of RGCs. Retinal ganglion cells (RGCs) were purified to >99.5% homogeneity from two- to three- litters of 5-day-old (P5) rat retinae by immunopanning as previously described. Briefly, retinae were digested with papain at 37° C. Following gentle trituration, cells were resuspended in a panning buffer containing insulin (5 µg/ml) and then incubated at room temperature with rabbit anti-macrophage antibodies. Retinal cells were incubated at room temperature sequentially on three immunopanning dishes: two coated with anti-rabbit secondary antibodies (to negatively select macrophages) and the third with T11D7 anti-Thy1 mAb. RGCs were released from the final panning dish with trypsin (Sigma).

To produce reaggregates, RGCs were plated at high density (>1,000 cells/µl) in 400 µl RGC growth medium in wells an 8-well chamber-slide (Nunc) coated with a surface that is not strongly adherent for RGCs (Permanox). One- to three-hours after plating, RGCs were resuspended gently to promote interaction and reaggregation, and this was repeated the following day. Following two days of culture at high density, reaggregates were collected and allowed to settle to separate them from dead RGCs, non-aggregated cells, and small reaggregates (<10 cells). Reaggregates were washed 3-6 times with 500 µl medium and evenly distributed on a number of PDL-laminin-coated coverslips in a small volume (50 µl per coverslip). Typically, an initial number of ~800,000 RGCs from 2-3 litters of rat pups was distributed in reaggregates over 24 coverslips. The following day, 450 µl medium was added to each well. RGC growth medium contained equal volumes of Neurobasal and. DMEM supplemented with B27, insulin, BDNF (50 ng/ml), CNTF (10 ng/ml), and forskolin as described previously (Meyer-Franke, A., Shen, S. & Barres, B. A. Astrocytes induce oligodendrocyte processes to align with and adhere to axons. Mol Cell Neurosci 14, 385-97 (1999)). ½ volume of medium was changed every 3-4 days for 10-14 days prior to addition of OPCs, during which time a dense bed of axons grew over the coverslip.

Purification of OPCs and maintenance of cocultures. Oligodendrocyte precursor cells (OPCs) were purified to >99.5% homogeneity from 7- to 8-day-old (P7-P8) rat brain cortices by immunopanning as previously described (Wang, S., Sdrulla, A., Johnson, J. E., Yokota, Y. & Barres, B. A. A role for the helix-loop-helix protein Id2 in the control of oligodendrocyte development. Neuron 29, 603-14 (2001)). Briefly, cerebral hemispheres were diced and digested with papain at 37° C. Following gentle trituration cells were resuspended in a panning buffer containing insulin (5 µg/ml) and then incubated at room temperature sequentially on three immunopanning dishes: Ran-2, anti-GalC, and O4. O4$^+$GalC$^-$ OPCs were released from the final panning dish with trypsin (Sigma). OPCs were seeded onto PDL-laminin-coverslips or coverslips containing 10- to 14-day-old RGC reaggregate cultures at a density of 40,000 OPCs per well in standard RGC growth medium containing equal volumes of Neurobasal and DMEM supplemented with B27, insulin, BDNF (50 ng/ml), CNTF (10 ng/ml), and forskolin as described previously. Cocultures were typically maintained for periods of 3-14 days as indicated, with ½ volume fresh medium changed every three days.

Purification of OPCs, early oligodendrocytes, and late oligodendrocytes. Eight P13 mouse brains were digested and dissociated as previously described (Segal, M. M., Baughman, R. W., Jones, K. A. & Huettner, J. E. in Culturing Nerve Cells (eds. Banker, G. & Goslin, K.) 309-338 (The MIT Press, Cambridge, Mass., 1998)). To isolate O4$^+$GalC$^-$ OPCs ("O4 cells"), one-third of the cells were subjected sequentially to the following immunopanning dishes: mouse anti-mouse Thy1.2, GalC, and O4. O4 cells were released from the final panning dish by trypsin (Sigma) and plated at 40,000 cells per well on 13-day-old RGC reaggregate cultures in the presence of absence of 1 µM DAPT (Calbiochem). To isolate early- and late- oligodendrocytes, the remaining two-thirds of dissociated cells were subjected sequentially to the following immunopanning dishes: BSL1 lectin (x2), rat anti-mouse PDGFRα, A2B5, anti-MOG clone 8-18C5 (x2), GalC. MOG$^+$PDGFRα$^-$ mature oligodendrocytes ("MOG cells") were released from the first MOG panning dish by trypsin (Sigma) and plated at 10,000 cells per well. GalC$^+$MOG$^-$ PDGFRα$^-$ early oligodendrocytes ("GC cells") were released from final panning dish by trypsin (Sigma) and plated at 20,000 cells per well. The differences in initial plating density helped to ensure an approximately equal density of MBP-expressing oligodendrocytes after six days.

Time-lapse microscopy. pEGFP-F (Clontech) is a plasmid that encodes for a membrane-targeted form (i.e., C-terminal farnesylation and palmitoylation sequences from c-Ha-Ras) of the enhanced green fluorescent protein under the control of the CMV promoter. The palmitoylation sequences are major determinants of sorting of proteins to myelin membranes (Schneider, A. et al. Palmitoylation is a sorting determinant for transport to the myelin membrane. J Cell Sci 118, 2415-23 (2005)). mCherry cDNA, encoding for a monomeric variant of the red fluorescent protein DsRed, was a gift from B. Baker (Stanford University) with the permission of R. Tsien (University of California at San Diego). To create a plasmid encoding for a membrane-targeted form of mCherry, the following primers were used to generate an mCherry PCR fragment containing AgeI and BsrGI restriction sites:

5'-AGCGCTACCGGTCGCCACCATGGTGAGCAAGGGCGAGGAG-3'

5'-GGATCCTTACTTGTACAGCTCGTCCATGCCGCCGG-3' pEGFP-F and the PCR product were digested with AgeI and BsrGl, and the resulting fragments purified from agarose gels and ligated by standard protocols (Qiagen).

For time-lapse microscopy of cocultures, RGC reaggregates were plated and PDL- and laminin-coated imaging dishes (MatTek) and maintained for 10-14 days prior to plating of transfected OPCs. OPCs were purified from P7-P8 rat brain and maintained in proliferation medium lacking B27 for 4-6 days prior to transfection. For each transfection, 3 million OPCs were trypsinized, collected, and resuspended in 100 µl nucleofector solution for OPCs (Amaxa) containing 2.0 µg pEGFP-F or mCherry-F plasmid. Electroporation was performed using program O-17 in an Amaxa Nucleofector, and OPCs were immediately plated on 10- to 14-day-old RGC reaggregate cultures on MatTek imaging dishes (120,000 cells per dish) in the presence of 1 µM DAPT.

Four- to six-day cocultures of GFP-F or mCherry-F-transfected OPCs and RGC reaggregates on MatTek imaging dishes were fed with fresh medium containing 1 µM DAPT and placed on a Nikon inverted microscope with an automated stage (Prior) and housing for temperature and $CO_2$ control. Temperature was maintained at 36.0° C. to prevent variance in temperature (typically ±1° C. over 24 hours) from overheating cells. Warmed and humidified gas (90% $O_2$: 10% $CO_2$) continuously flowed into the imaging chamber to maintain pH of the medium. Wavelength-specific filters for excitation (~490 nm max for GFP and ~570 nm max for mCherry) were incorporated into the lamp housing for automation. To avoid excess movement around the stage, a common emission filter (Chroma Cat. No. 52006) was used for both the green and red channels. Images were collected used a Cascade:1K CCD camera with an on-chip multiplication gain function to minimize exposure times and therefore phototoxicity. Typical exposure times were 50 ms to 200 ms (with a gain setting of 3500) every 10 min, depending on the level of expression of the fluorescent protein in the cell of interest. Movies and tracked cells were acquired and analyzed using Metamorph 2.0 software. The starting and ending images of cells that were either imaged every 10 min and/or simply "tracked" once per day, with the majority of cells examined at two timepoints 20-24 hours apart (range=16-48 hrs). Images and movies were examined for the formation of new stable myelin segments from non-myelinating and myelinating oligodendrocytes. In some cases, a single cell contributed to both types of data, beginning as a non-myelinating oligodendrocyte for the first day of tracking and, having formed myelin in that period, being defined as a myelinating cell for the next day of analysis.

Immunostaining. Immunostaining of cocultures was performed using standard protocols essentially as previously described with one additional drying step. Briefly, cocultures were gently fixed with 4% PFA for 10 min at room temperature, rinsed with PBS, and air-dried extensively to prevent shifting and peeling of cultures from the coverslip surface during staining. Fixed and dried cultures were blocked with 50% normal goat serum in antibody buffer containing 0.4% Triton X-100 for permeabilization. Primary antibodies were added either overnight at 4° C. or for 90 min at room temperature in a buffer containing 10% normal goat serum and 0.08% Triton. Following rinsing with PBS, cultures were incubated with Alexa 488-, Alexa 594-, and/or Alexa 680- labeled secondary antibodies (1:1000, Molecular Probes) for 45 min at room temperature. Coverslips were rinsed gently, mounted on slides using Vectashield with DAPI, and sealed with nail varnish.

Antibodies used in this study included: rabbit anti-NG2 (1:500; Chemicon), mouse anti-MBP (1:100; Chemicon), rat anti-MBP (1:100, Abcam), mouse anti-GFAP (1:2000, Sigma), mouse anti-pan-sodium channel (1:5000; gift of J. Trimmer), rabbit anti-Caspr (1:500; gift of E. Peles), and goat anti-Notch1 (1:1000; R&D Systems).

Conditional knockout cells and infection with AdCre. OPCs were purified from P9 Notch1 conditional knockout (gift of A. Rosenthal, Genentech) and presenilin double conditional knockout (gift of Jie Shen, Brigham and Women's hospital) mouse brains by a slight modification of the panning protocol for rat cells as described previously. The first panning dish was coated with mouse anti-mouse Thy1.2 (Serotec) rather than Ran-2. Mouse OPCs were plated on PDL-coated flasks in defined proliferation medium (DMEM supplemented with B27, insulin, 10 ng/ml PDGF, 1 ng/ml NT3, 10 ng/ml CNTF, and forskolin) for 2 days and then passaged onto PDL-coated tissue culture plates at a density of 1 million cells per plate. One hour after plating, OPCs were infected in a small volume of proliferation medium with B27 (4 ml) at a multiplicity of infection (MOI) of 10 with AdCre, an adenovirus encoding the Cre recombinase, or AdEmpty, a control virus (University of Iowa Gene Transfer Vector Core). The following day, OPCs were passaged onto PDL-coated coverslips or 10- to 14-day-old RGC reaggregate cultures at a density of 40,000 cells per well (24-well plate).

Electron microscopy. Electron microscopy was performed at The Cell Sciences Imaging Facility at Stanford University Medical Center. Briefly, purified P8 rat RGC reaggregates and 20,000 purified brain P8 OPCs were embedded in Matrigel (1:2 with RGC growth medium) and plated on PDL-coated coverslips. RGC growth medium was initially supplemented with PDGF (10 ng/ml) and NT3 (1 ng/ml) to maintain the proliferation and migration of OPCs within the Matrigel during the initial outgrowth of RGC axons. Cocultures were fed ½ volume every 3 days without added PDGF and NT3. After 27 days, cocultures were fixed in 2% glutaraldehyde in sodium cacodylate buffer at 4° C. Following treatment with 1% osmium tetroxide and 1% uranyl acetate, samples were embedded in epon. Sections were taken between 75-90 nm, picked up on formvar/carbon coated 75 mesh Cu grids, stained for 20 seconds in 1:1 super-saturated uranyl acetate in acetone followed by staining in 0.2% lead citrate. Images were acquired with the JEOL 1230 TEM at 80kV.

Example 2

Genetic Inhibition of γ-Secretase

Active γ-secretase is a complex of four proteins, of which presenilin (PS) is thought to provide the active site. A knockdown of presenilin-1 and presenilin-2 expression in OPCs is shown to have the same effect on myelination as DAPT. These data demonstrate that DAPT is acting through gamma-secretase; and that the relevant activity is in oligodendrocytes.

OPCs were transfected with either 1.5 μg siCONTROL (i.e., non-targeting siRNA) or 1.0 μg siRNA targeting PS1 and 0.5 μg siRNA targeting PS2. These constructs target expression of a protein required for g-secretase activity. Because our gene chip studies demonstrate that both RGCs and OPCs (and OLs) express both PS-1 and PS-2, siRNAs were chosen to inhibit the activity of both presenilins. Transfected OPCs were plated immediately on ten-day-old cultures of RGC reaggregates, and in some cases in the presence or absence of 1 μM DAPT. Myelination was examined after six days by MBP immunostaining, determining the proportion of double-labeled MBP-positive cells that are myelinating. As expected, the transfected cells displayed enhanced myelination.

These data demonstrate that genetic agents that inhibit γ-secretase activity are also effective at enhancing myelination.

Example 3

The effect of blocking γ-secretase activity in vivo is examined. DAPT (100 mg/kg s.c.) is administered daily to perinatal rats. Myelination is examined at P6, a time point at which only a very small number of OLs and myelin segments in control rats (injected with vehicle alone) are observed. Specifically, pairs of optic nerves from these rats are cryosectioned and immunostained for CC1 and MBP to determine if there are differences in the numbers of mature oligodendrocytes or myelin segments. Indications of changes in myelination are followed by Western blots and immunostaining for a-neurofilament, to ensure that the numbers and morphologies of axons are unaffected.

What is claimed is:

1. A method of enhancing CNS myelination in a patient having a CNS disorder characterized by a myelin deficiency, the method comprising:

contacting an oligodendrocyte or progenitor thereof in the proximity of an axon in a patient having a CNS disorder characterized by a myelin deficiency with an effective dose of an inhibitor of γ-secretase;

wherein the myelination of said axon is enhanced in said patient.

2. The method according to claim 1, wherein said inhibitor of γ-secretase is a genetic agent.

3. The method according to claim 1, wherein said inhibitor of γ-secretase is a pharmacologic agent.

4. The method according to claim 1, wherein said CNS disorder characterized by a myelin deficiency is a demyelinating disorder.

5. The method according to claim 4, wherein said demyelinating disorder is multiple sclerosis.

* * * * *

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Synthetic Primer

<400> SEQUENCE: 1
agcgctaccg gtcgccacca tggtgagcaa gggcgaggag                              40

<210> SEQ ID NO 2
<211> LENGTH: 35
<212> TYPE: DNA
<213> ORGANISM: Artificial Sequence
<220> FEATURE:
<223> OTHER INFORMATION: Synthetic Primer

<400> SEQUENCE: 2
ggatccttac ttgtacagct cgtccatgcc gccgg                                   35
```